United States Patent
Cox et al.

(10) Patent No.: US 7,850,740 B2
(45) Date of Patent: Dec. 14, 2010

(54) INDIRECT SKELETAL COUPLING AND DYNAMIC CONTROL OF PROSTHESIS

(75) Inventors: Brian N. Cox, Thousand Oaks, CA (US); Mohsen Khoshnevisan, Newbury Park, CA (US); Douglas G. Smith, Edmonds, WA (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 72 days.

(21) Appl. No.: 12/062,227

(22) Filed: Apr. 3, 2008

(65) Prior Publication Data

US 2009/0254196 A1 Oct. 8, 2009

(51) Int. Cl.
*A61F 2/78* (2006.01)
*A61F 2/80* (2006.01)
(52) U.S. Cl. .......................... 623/37; 623/33
(58) Field of Classification Search .......... 623/32–37, 623/11.11, 16.11, 18.1, 2
See application file for complete search history.

(56) References Cited

U.S. PATENT DOCUMENTS

| | | | | |
|---|---|---|---|---|
| 4,743,264 | A * | 5/1988 | Sherva-Parker | 623/33 |
| 5,062,855 | A * | 11/1991 | Rincoe | 623/24 |
| 5,425,763 | A * | 6/1995 | Stemmann | 623/11.11 |
| 5,507,835 | A * | 4/1996 | Jore | 623/36 |
| 5,879,386 | A | 3/1999 | Jore | |
| 6,273,918 | B1 * | 8/2001 | Yuhasz et al. | 623/33 |
| 6,387,096 | B1 * | 5/2002 | Hyde, Jr. | 606/60 |
| 7,101,374 | B2 * | 9/2006 | Hyde, Jr. | 606/60 |
| 7,347,874 | B2 * | 3/2008 | Disilvestro | 623/18.12 |
| 2009/0112263 | A1 * | 4/2009 | Pool et al. | 606/246 |

OTHER PUBLICATIONS

M. De Cuyper, et al., "Synthesis of Magnetic Fe304 Particles Covered With a Modifiable Phospholipid Coat", J. Phys.: Condens. Matter, 2003, pp. S1425-S1436, 28.

I. Esformes, et al., "A Magnetically Augmented Elbow Prosthesis: Design and Biomechanical Evaluation", Bulletin for the Hospital for Joint Diseases Orthopaedic Institute, pp. 69-80, 41.

J. M. Kartush, et al., "Electromagnetic Ossicular Augmentation Device", Otolaryngologic Clinics of North America, Feb. 1995, pp. 155-172, 28:1.

(Continued)

*Primary Examiner*—William H Matthews
*Assistant Examiner*—Jacqueline Woznicki
(74) *Attorney, Agent, or Firm*—Glenn H. Lenzen; Polsinelli Shughart PC (57) ABSTRACT

Provided is a prosthesis system for indirectly coupling a prosthesis to the skeletal structure of a person. The system includes a plurality of individual magnets and magnet sets attached to a prosthetic socket of a prosthetic device. The magnets may be permanent magnets or electromagnets. A second plurality of magnets is embedded within a residual limb of a person, mounted to or within a sub-dermal strut. In operation, the magnetic fields generated by the magnets of the prosthetic socket, which may be dynamic magnetic fields, interact with the magnetic fields generated by the magnets anchored beneath the skin of the person, to hold the prosthetic device in position during use. A power supply provides current to any electromagnets, and a controller alters any required magnetic fields based on input received from both load and position sensors in the sub-dermal strut.

13 Claims, 5 Drawing Sheets

OTHER PUBLICATIONS

M. A. Riley, et al., "Magnets in Prosthetic Dentistry", Journal of Prosthetic Dentistry, Aug. 2001, pp. 137-142, 86.

P. R. Ros, et al., Hepatic MR Imaging with Ferumoxides: A Multicenter Clinical Trial of the Safety and Efficacy in the Detection of Focal Hepatic Lesions, Radiology, Aug. 1995, pp. 481-488, 196.

A. D. Walmsley, et al., "Magnet Retained Overdentures Using the Astra Dental Implant System", British Dental Journal, Jun. 5, 1993, pp. 399-404, 174.

R. Weissleder, et al., "Superparamagnetic Iron Oxide: Pharmacokinetics and Toxicity", AJR, Jan. 1989, pp. 167-173, 152.

* cited by examiner

INDIRECT SKELETAL COUPLING AND DYNAMIC CONTROL OF PROSTHESIS

FIELD OF THE INVENTION

This invention relates generally to prosthetic devices. More particularly, to a prosthetic device magnetically and dynamically interfaced with the skeletal structure of a person, to affix the prosthetic device in position and control the distribution and magnitude of interactive forces.

BACKGROUND

As the functionality of extremity prostheses is advanced, increasing loads will be induced into the total prosthesis system. These loads must be isolated from the residual limb of the person, or alternatively reacted into the appendage or amputation point of the residual limb in a controlled manner. Many current prosthetic devices, which are often a socket-type arrangement, shed their loads principally into the skin of an appendage or into the skin of a torso, via belt-strap-buckle attachments or other mechanical fastening devices. Significant loading of the skin typically provides an inferior mechanical foundation for the prosthesis system. An inferior mechanical foundation may prove inadequate for the prosthesis to function properly, or too compliant to support the induced loads. Further, conventional systems create discomfort for the person, damage the skin, and/or permanently stretch the skin. Using belts, straps, etc. that pass around the torso or appendage of a person results in a large, bulky, heavy and uncomfortable prosthesis system that creates an unnatural appearance that is strongly disfavored by the wearer. Compliance of existing systems is typically too high, resulting in unwanted and uncontrolled prosthesis slip during use, even with relatively lightly loaded prostheses.

The human skeleton supports loads from the extremities of the body, therefore, when the loads can be properly translated to the skeletal structure a more robust prosthesis system can be envisioned. Osseointegration is a natural response of the body that can help with this load translation, thereby addressing at least some of the mechanical deficiencies associated with current prosthesis systems. With osseointegration, foreign objects introduced into the body (for example a titanium implant placed into a cavity of a bone such as the femur) are not only accepted by the body and brain, but become an integral part of the body structure.

The genetic codes within the body that typically would direct the body to reject the foreign object are not, in fact, activated. Instead, bone cells attach to the surface of the foreign object (e.g. titanium implant) resulting in a firm and permanent anchorage of the implant to the bone. Unfortunately, existing prosthetic devices that capitalize on the natural phenomenon of osseointegration typically involve a permanent and constant penetration of the skin. Permanent skin penetration often leads to short and long term infection issues, requiring enhanced care by the individual.

While there are existing systems that employ magnetic materials and devices implanted below the patient's skin, these devices are not typically designed to robustly and magnetically couple the prosthetic device to the residual limb, while controlling multiple loads from multiple orientations. One such device known in the prior art is U.S. Pat. No. 5,879,386 to Jore, "Magnetic Prosthesis System". The need to use straps, buckles, etc. to affix the prosthesis to the appendage, and to control prosthesis movement, is still present. Further, the permanent magnetic fields established by implanted magnetic materials and magnets within a prosthesis cannot adapt and change to varying loads and functional movements of the prosthesis.

Hence there is a need for a prosthesis system to address one or more of the drawbacks identified above.

SUMMARY

The prosthesis system herein disclosed advances the art and overcomes problems articulated above by providing a prosthetic device indirectly coupled to the residual limb of a person through the use of controlled, dynamic magnetic forces and minimal mechanical coupling.

In particular, and by way of example only, according to an embodiment, provided is a prosthesis system including: an implant structured and arranged to permanently integrate with a residual limb, the implant having at least one sub-dermal strut; a prosthetic limb having a prosthetic socket, the socket having a base; at least one magnet pair for countering an axial load, the pair having a first magnet attached to the sub-dermal strut and a second magnet attached to the base, the first and second magnets aligned to repel one another and resist contact between the residual limb and the prosthetic socket; at least one magnet pair for minimizing a lateral force, the pair having a third magnet attached to the sub-dermal strut and a fourth magnet attached to the prosthetic socket, the third and fourth magnets aligned to repel one another; and at least one magnet set for minimizing the lateral force and stabilizing axial load displacements, the set having a fifth and a sixth magnet aligned on the prosthetic socket and a seventh magnet attached to the sub-dermal strut, the seventh magnet positioned within a magnetic potential well formed by the sixth and seventh magnets.

In another embodiment, provided is a prosthesis system including: a repelling means for magnetically repelling an axial load; a minimizing means for magnetically minimizing axial load displacements; and a resisting means for magnetically resisting a rotational load.

In still another embodiment, provided is a method for implementing a prosthetic device, including: securing to a residual limb of a person, beneath a skin, an implant having a sub-dermal strut; attaching to the sub-dermal strut a plurality of discrete magnets; and presenting a prosthetic socket having an array of individual magnets and magnet sets wherein an individual magnet of the prosthetic socket aligns with a first discrete magnet of the sub-dermal strut to counter an axial load, and further wherein a magnet set of the prosthetic socket and a second discrete magnet of the sub-dermal strut interact to secure the prosthetic socket in position and to counter lateral loads and axial load displacement.

In yet another embodiment, provided is an implant for a prosthetic device, including: an anchoring post for interfacing the implant with a remnant bone of a residual limb; and at least one sub-dermal strut wherein a magnet attached to the sub-dermal strut is positioned a distance from the remnant bone, in proximity to a surface of a skin.

DETAILED DESCRIPTION

Before proceeding with the detailed description, it should be noted that the present teaching is by way of example, not by limitation. The concepts herein are not limited to use or application with one specific type of magnetically coupled and dynamically controlled prosthetic device. Thus, although the instrumentalities described herein are for the convenience of explanation, shown and described with respect to exemplary embodiments, the principles herein may be equally applied in other types of magnetically coupled and dynamically controlled prosthetic devices.

Figure 1:
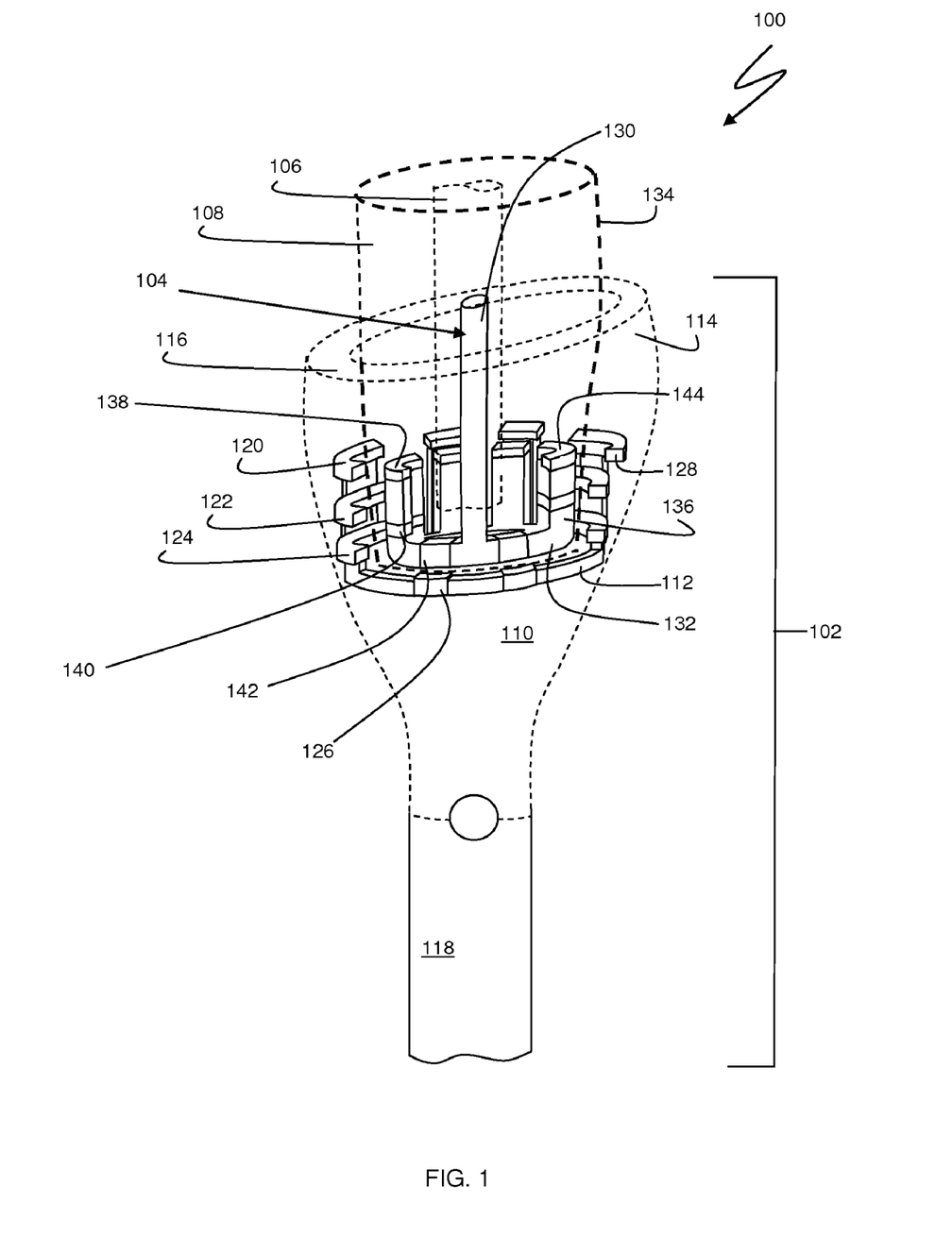
FIG. 1 is a perspective view of a prosthesis system, according to an embodiment.

Referring initially to the perspective view of FIG. 1, a prosthesis system 100 in accordance with the present disclosure is presented. The prosthetic device or prosthesis 102 and related coupling mechanisms are not limited to a single type of prosthetic device, and may include any number of prosthetic designs well known in the art, to include partial limb prosthesis, whole limb prosthesis, and orthopedic correction prosthesis. As shown in FIG. 1, an implant or implant device 104 may be surgically and permanently anchored or attached to the skeleton of a person. More particularly, in at least one embodiment of the present disclosure, implant device 104 may be anchored to a remnant bone 106 of a residual limb 108. As discussed in greater detail below, indirect coupling of prosthesis 102 to residual limb 108 is achieved primarily through the generation and control of magnetic forces that interact to repulse components of system 100 away from one another while simultaneously locking prosthesis 102 in position. While some contact between prosthesis 102 and residual limb 108 may occur or be required, the contact is minimal and incidental to the primary, magnetic coupling. In this manner, prosthesis 102 may be held in a required position(s) with adequate stability to facilitate use, while at the same time provide for movement and adjustment of prosthesis 102 in response to forces reacted into, through or by residual limb 108. The indirect coupling of prosthesis 102 provides for the elimination of cumbersome, heavy and often times uncomfortable attachment straps, harnesses, buckles, etc.

Considering prosthesis system 100 in detail, prosthesis 102 includes a prosthetic socket 110 having a rigid structure 112. In at least one embodiment, prosthetic socket 110 may include a sleeve or receptacle 114 formed by a perimeter wall 116. Wall 116 may be substantially cylindrical in shape, as represented in FIG. 1, or alternatively it may be formed into any number of shapes consistent with the size, shape and orientation of residual limb 108. Sleeve 114 may provide rigid structure 112 protection and isolation from external elements and from damage, and may assist in the coupling of rigid structure 112 with a prosthetic limb 118. Further, sleeve 114 may present an appearance resembling that of a natural appendage or of a standard prosthetic device. Alternatively, rigid structure 112 may have little or no outer covering or sleeve, and may be mechanically coupled with prosthetic limb 118 by any means well known in the art.

Rigid structure 112 may include a plurality of magnets, of which magnets 120, 122, 124, 126 and 128 are exemplary. Magnets 120-128 may be attached to or mounted on rigid structure 112, or they may be integral to the structure 112. The magnets may be considered and classified as individual magnets, such as magnets 120, 126, and 128, or they may be part of a magnet set, such as magnets 122 and 124, which form a magnet set. Cross-referencing for a moment FIG. 1 with FIG. 2, it is apparent that the magnetic fields of magnets 120-128 are oriented in the same direction for all magnets, which is to say generally toward implant device 104. Using a conventional nomenclature for magnetic classification, it can be said that each magnet 120-128 has the same magnetic pole (e.g. North or South) oriented in generally the same direction, i.e. inward.

The number of individual magnets or magnet sets positioned on or within rigid structure 112 may be tailored depending on the size of prosthetic device 102, the anticipated number, types and orientations of forces reacting on prosthetic system 100, and the control mechanism employed. The types of magnets used can vary, as well. For example, permanent magnets (bar or otherwise) may be used exclusively for all magnets 120-128. Alternatively, magnets 120-128 may all be electromagnets. Yet again, a combination of electromagnets and permanent magnets may be employed. As can be appreciated by those skilled in the art, an advantage to electromagnets is that both the orientation and magnetic field strength can be dynamically controlled and modified by varying the electric current applied to the magnets. In the case of electromagnets, a control system such as that described in greater detail below may be used to drive and control the magnets. Control and modification of the magnetic field generated by a permanent magnet, however, may be effected by a physical change in the position or orientation of the magnet. Magnets 120-128 may be constructed of materials such as cobalt-samarium, cobalt-rare earth metals, or other magnetic/paramagnetic materials.

Referring once again to FIG. 1, implant device 104 includes an anchoring post 130 for interfacing implant 104 with the remnant bone 106 of residual limb 108. Anchoring post 130 is, in at least one embodiment, surgically and permanently anchored to remnant bone 106. Anchoring post 130 may be inserted directly into or otherwise attached to a section of remnant bone 106. For example in a partially amputated or damaged leg, the bone may be the femur. Through a process known as osseointegration, the "foreign" object or implant 104/post 130 inserted into and around the bone becomes part of the leg. The implant 104/post 130 is "accepted" by the body of the person and the remnant bone 106 permanently adheres to the implant 104/post 130. There are several advantages to this approach. The entire implant 104/post 130 may be inserted under the skin of the person, thereby eliminating the need for any structure or body part to extend through the skin to the outside environment. This approach, in turn, reduces the risk of both short and long-term infection. Further, once the body begins to adhere to and accept the implant 104/post 130 as "non-foreign" matter, the resulting structural integrity of system 100 is enhanced.

Anchoring post 130 interfaces with, attaches to, and/or includes one or more struts or plates projecting from remnant bone 106 and passing along the sub-dermal layer beneath the skin, of which sub-dermal strut 132 is exemplary. As shown in FIG. 1, sub-dermal strut 132 is positioned beneath, but in close proximity to, the skin 134 of residual limb 108, in the sub-dermal region of the limb 108. The structure of sub-dermal strut 132 may include a single flange or extension 136, or it may include multiple flanges, as shown in FIG. 1, without departing from the intent and scope of the present disclosure.

Positioned on one or more flange of sub-dermal strut 132 is a plurality of discrete permanent magnets, of which magnets 138, 140, 142 and 144 are exemplary. Each discrete magnet 138-144 is positioned to ultimately align with one or more individual magnets (120, 126, 128) or magnet sets (122 & 124) of rigid structure 112, such that the interaction of magnets attached to rigid structure 112 and sub-dermal strut 132 controls the position of prosthetic socket 110 relative to residual limb 108 as system 100 is implemented.

Figures 2, 3:
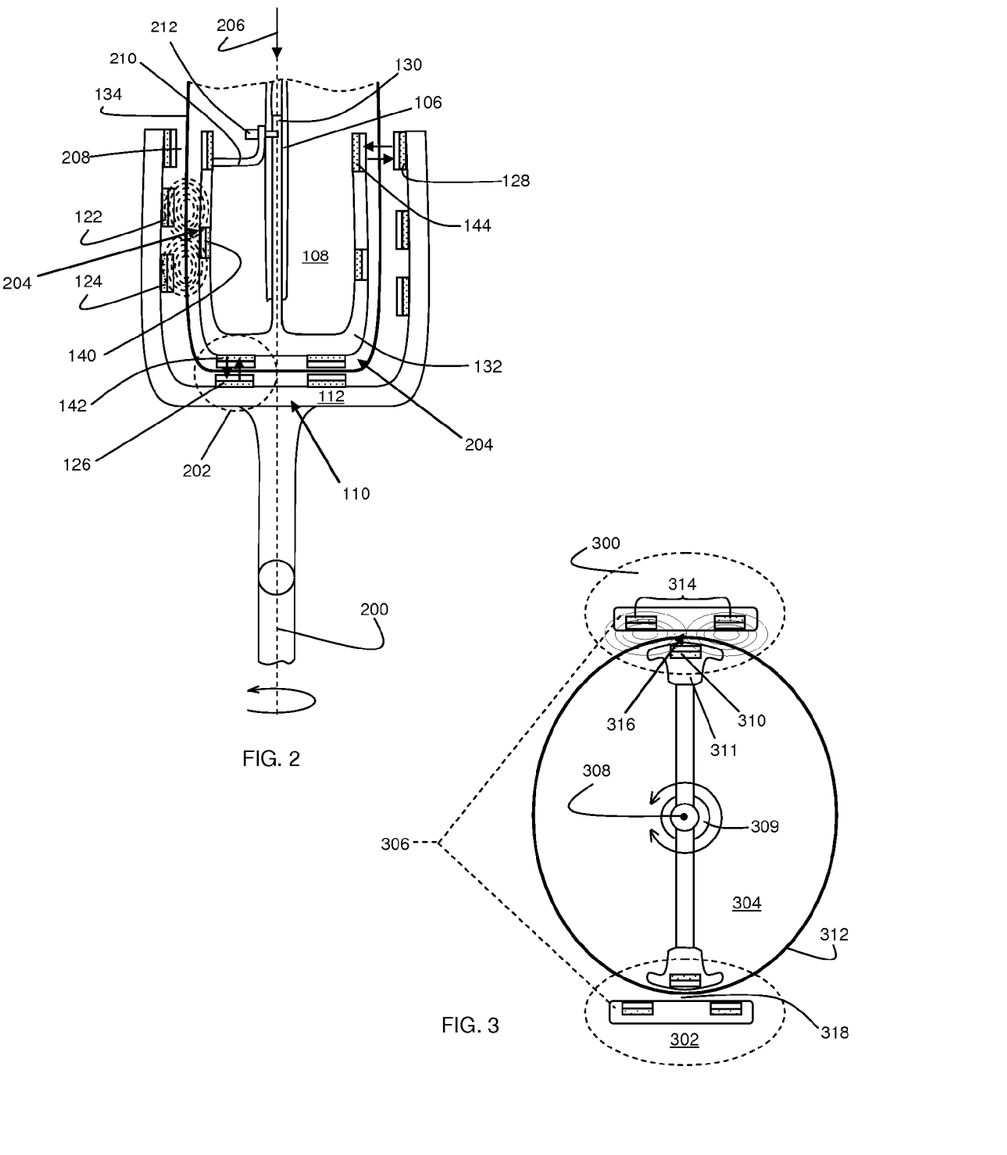
FIG. 2 is a cross-sectional view of a prosthesis system, according to an embodiment.
FIG. 3 is a top view of a portion of a coupled prosthetic device and appendage, according to an embodiment.

The physical relationship and magnetic force interactions of the magnets (120-128 and 138-144) of system 100 are best represented and understood by referring once again to FIG. 2. In FIG. 2, anchoring post 130 is anchored to remnant bone 106. Rigid structure 112 includes individual magnet 128 positioned opposite from and aligned with discrete magnet 144 of sub-dermal strut 132. A specified magnetic pole (be it North or South) of magnet 128 is facing toward the same magnetic pole of magnet 144, such that the magnets 128, 144 repel one another as the magnets are aligned and the distance between the magnets 128, 144 is reduced. The arrows of FIG. 2 associated with the magnet pair (magnets 128 and 144) represent the opposing and repelling magnetic forces of the two magnets 128, 144. The interaction of the two magnets 128, 144, and similarly situated magnet pairs about the circumference or perimeter of system 100, works to minimize lateral forces or loads, including rotational forces (as represented by rotation about axis 200), exerted on residual limb 108 and/or prosthetic socket 110. Minimizing such lateral loads helps to minimize or eliminate undesired or uncontrolled lateral displacements. While some degree of lateral displacement may be allowed and even desired, significant displacements resulting from lateral loads may be avoided.

Rotational loads, and the rotation of either prosthetic socket 110 and/or residual limb 108, are also minimized and controlled by the interaction of magnet sets and discrete magnets, such as the magnet pair 122-124 and discrete magnet 140. As shown in FIG. 2, the magnetic fields of magnets 122 and 124 act to generate a "magnetic potential well" 204 in which magnet 140 may be positioned. The effect of positioning magnet 140 in the "magnetic potential well" is to "lock" magnet 140 in place, thereby preventing lateral displacements in the form of rotation about axis 200. Other lateral displacements which may or may not have a rotational component may also be minimized or eliminated in this manner.

Referring for a moment to FIG. 3, a top view of a partial prosthesis system of the present disclosure is presented. It can be appreciated that the use of multiple magnet set-discrete magnet combinations, e.g. combinations 300 and 302, can help to secure and position a residual limb 304 relative to a rigid structure 306 of a prosthetic socket. Stated differently, rotation or circumduction (of either residual limb 304 or rigid structure 306) about axis 308 (shown as a center-line of a bone remnant 309) can be minimized or eliminated by the use of multiple magnet set-discrete magnet combinations 300, 302. Still referring to FIG. 3, and consistent with the discussion above, the position of a discrete magnet (e.g. magnet 310 of sub-dermal strut 311) relative to the skin 312 of residual limb 304, as well as the close proximity of discrete magnet 310 and magnet set 314, is clearly disclosed. As noted above, magnet 310 resides in the sub-dermal region of limb 304, and its location relative to rigid structure 306/magnet set 314 is important to maintain position control. Position control is achieved by positioning magnet 310 in the "magnetic potential well" 316 formed by the magnets of magnet set 314.

Referring once again to FIG. 2, a magnet pair includes an individual magnet 126 of rigid structure 112 positioned opposite a discrete magnet 142 integral to sub-dermal strut 132. Discrete magnet 142 is located at substantially the distal end 204 of residual limb 108. The magnets 126, 142 are aligned to ensure a magnetic field generated by the first (e.g. magnet 126) repels a corresponding field generated by the second (e.g. magnet 142), as represented by the arrows stemming from the two magnets 126, 142. As can be appreciated, like poles of each magnet face one another to create the necessary repulsion force.

As highlighted in FIG. 2, the repulsion of magnet 142 by magnet 126, and the performance of similarly situated magnet pairs of system 100, acts to resist an axial load (e.g. gravitational load, weight, impact load) acting generally along axis 200, as represented by arrow 206. Resistance to the axial load results in residual limb 108, sub-dermal strut 132 and magnet 142 being positioned in close proximity to, but not in contact with, prosthetic socket 110. In addition to properly positioning prosthesis 102 for use, the "suspension" of residual limb 108 just "above" rigid structure 112 prevents damage/injury to skin 134 resulting from contact with rigid structure 112.

The magnets of prosthetic socket 110 may be any of a type well known in the art, and as discussed above may be permanent magnets or electromagnets. Further, the magnets may be manufactured from a variety of well known ferromagnetic/magnetic materials. Magnets may be chosen based on an optimization of design considerations, to include hysteresis effects, demagnetization, and rotation of the magnetization. Additionally, the magnets attached/integral to sub-dermal strut 132 may be shaped and tailored to fit the contour of the sub-dermal layer or bone structure of the person. Tailoring the shape of the magnets may allow for minimal separation between structure magnets and sub-dermal magnets. Also, the magnets of the sub-dermal strut, as well as the strut itself and other implanted structures, must be manufactured from biocompatible materials. For example, implanted structures may be manufactured from materials such as Ti-6Al-4V.

Still referring to FIG. 2, one or more sub-dermal struts, e.g. sub-dermal strut 132, may be mechanically anchored to remnant bone 106 via a stiffening strut 210 or, in the case of the femur bone, a femoral anchor, of a type well known in the art. Stiffening strut 210 is attached to the relevant bone structure using a screw, post or other attachment mechanism 212.

As can be seen in FIGS. 1-3, there may be a gap or air gap between the magnets (individual and magnet sets) of a rigid structure, e.g. structure 112 and the surface (skin) of the residual limb, e.g. limb 108 (e.g. gap 208 in FIG. 2 or gap 318 in FIG. 3). The air gap is intended to provide a non-structural separation between a hard surface, such as a magnet or rigid structure and the soft tissue of the skin. In this way, the skin is protected from damage that traditionally occurs when a prosthetic device, in contact with the skin, moves or is displaced relative to the skin. The air gap is established by: (a) the physical separation of hardware designed into system 100; and (b) the off-setting, opposite repulsion forces that "suspend" prosthetic socket 110 a predetermined distance away from the surface of residual limb 108.

Figure 4:
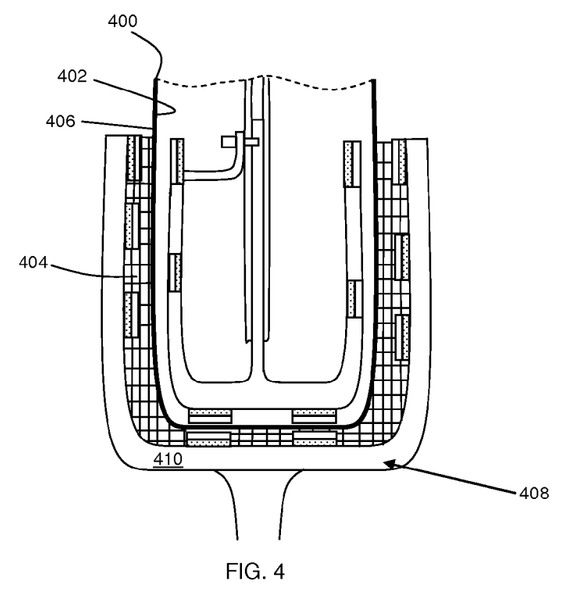
FIG. 4 is a cross-sectional view of a prosthesis system, according to an embodiment.

Maintaining a stable air gap using magnetic forces may not always be desirable or necessary. Referring now to FIGS. 4-7, an embodiment of the present application is disclosed wherein the air gap (e.g. air gap 318 in FIG. 3) is no longer present. In this embodiment of system 100, a hybrid solution is presented having both magnets and a skin-contacting material that work in concert to maintain stability and transmit loads both mechanically and magnetically. In particular, as shown in FIG. 4, a soft socket liner 400 occupies much, if not all, of the space previously reserved for an air gap. The liner 400 contacts the skin along one surface 402, while interfacing with a compliant coupling layer, material or structure 404 along another 406. Socket liner 400 differs from conventional liners in that it is mechanically coupled to the compliant coupling material 404. Mechanical coupling, however, may or may not include some form of adhesion. For example, in at least one embodiment the mechanical coupling of liner 400 and material 404 is through frictional forces alone. In this way, liner 400 may be applied to a residual limb (e.g. limb 108 in FIG. 1) in a well known and simplistic manner, i.e. akin to unrolling a sock. Compliant coupling material, as part of prosthetic socket 408, may then easily slide over the liner 400 during the donning and doffing processes.

Figures 5, 6, 7:
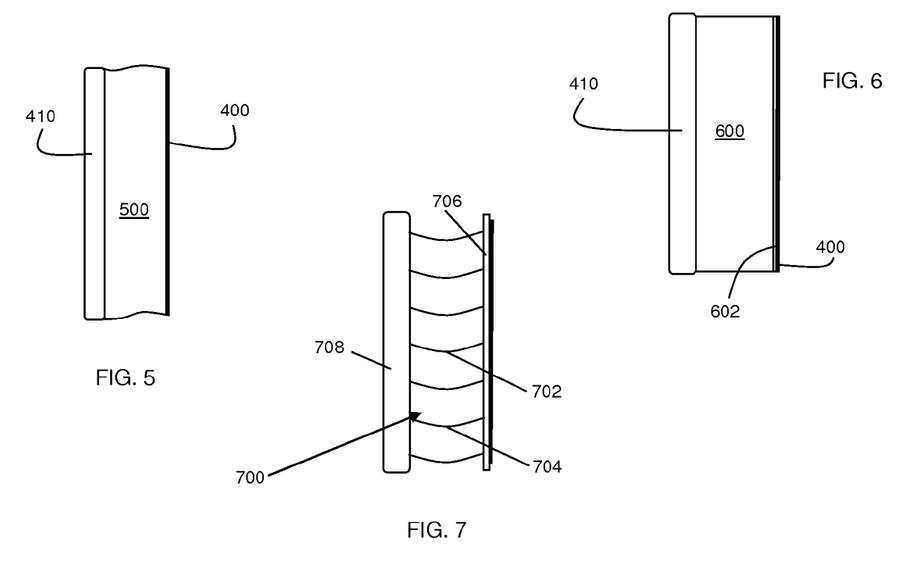
FIG. 5. is a cross-sectional view of a compliant coupling material, according to an embodiment.
FIG. 6. is a cross-sectional view of a compliant coupling material, according to an embodiment.
FIG. 7. is a cross-sectional view of a compliant coupling material, according to an embodiment.

Considering for a moment FIGS. 5-7, several different configurations of compliant coupling material 404 are presented. Material 404 may include a fluid or gel bladder 500 (FIG. 5) sandwiched between a rigid structure 410 and socket liner 400. Alternatively, material 404 may be an elastomer or foam (to include open cell foam) material 600. In this embodiment, as well as in others, a lubricating interface or layer 602 may serve to control the frictional forces between socket liner 400 and the compliant material 600. In yet another embodiment of the present disclosure, compliant coupling material 700 may be a compliant truss structure. Specifically, material 700 may include shaped struts (e.g. wires) connecting two layers in a "sandwich" type construction. For example, as shown in FIG. 7, connecting wires, of which wires 702 and 704 are exemplary, connect a pressure sheet 706 at one end with a rigid or semi-rigid frame 708 at the other. Frame 708 may be the rigid structure onto which magnets are mounted (e.g. rigid structure 410 in FIG. 4), or in one embodiment frame 708 is a separate component attached or adhered to the rigid structure.

Compliant coupling materials 700 that allow air to diffuse to the skin are one important class of material to be considered. Similarly, since the magnetic coupling system 100 comprises very carefully defined arrays of magnets (individual magnets, discrete magnets and magnetic pairs), the rigid structure (e.g. structure 410 in FIG. 4) that supports the individual magnets and magnet pairs may, in at least one embodiment, consist mainly of struts or supports separated by open space. The compliant coupling material 700, therefore, need not cover the entire surface of the corresponding skin-contacting socket liner (e.g. liner 400, FIG. 4), but only those regions opposing a strut or support of the rigid structure. The remaining open space will assist in allowing air to reach the skin.

It is possible that certain metal materials or magnetic forces external to system 100 may impact the magnetic interaction of system 100 magnets. As such, a shielding cover (not shown) may be employed to isolate system 100 magnets from external metals and external magnetic forces.

The system 100 of the present disclosure must control six degrees of freedom or relative displacement between a residual limb and the prosthetic device: three in translation and three in rotation. The largest forces addressed by system 100 are primarily transmitted magnetically (without loading the soft tissue of the residual limb), while smaller forces (e.g. anterior-posterior and medial-lateral), as well as forces needed to maintain positional stability, are transmitted through a skin-contacting socket liner and coupling material such as that discussed above.

The largest forces arise from displacement along an axis of a limb, especially the gravitational load of the person's body weight as well as the weight of the prosthetic device when the limb is raised. Other substantial loads are the circumduction torque (rotation about the axis of the limb) and torques about one or more axis normal to the axis of the limb. These loads are primarily transmitted magnetically. Other loads (from the other degrees of freedom of displacements) may be transmitted mechanically or via a combination of magnetic forces and skin tractions.

The coupling between rigid structure and soft tissue (residual limb) will transfer smaller loads. The coupling mechanism, to include the compliant coupling material, will address load transfer characteristics that are unique to the magnetic force transmission system of the present disclosure and are not present in current conventional systems. More specifically, the coupling must shield the skin-contacting liner (socket liner) from displacements of the rigid structure (of the prosthetic socket) about its equilibrium position which, in normal use, are permitted by the nature of magnetic interactions. These displacements or oscillations will typically be several millimeters and may be very frequent. The displacements could, if not addressed, cause tissue breakdown and damage if allowed to reach the skin. Shielding of the skin can be achieved by ensuring that the compliant coupling material is compliant in shear.

Additionally, the coupling of compliant material and socket liner should maintain a preferred normal separation of the skin and the rigid structure of the prosthetic socket, to control lateral displacements out of the equilibrium position. The coupling mechanism (and related materials) should also exhibit plasticity under normal overloads, so that it can serve as a shock-absorbing protective layer during accidental impact. Optimization of the coupling mechanism may be achieved after the magnitudes of the forces to be reacted are known. Further, each system 100 of the present application may be custom designed to fit and work for a particular person having a particular loss or partial loss of a limb.

Figure 8:
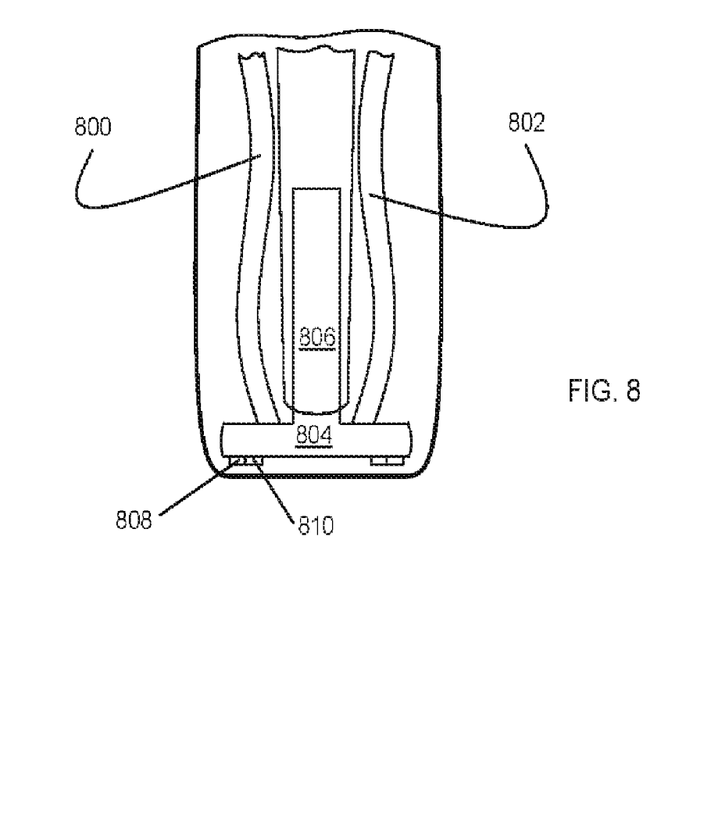
FIG. 8 is a cross-sectional view of a portion of a prosthetic implant and appendage with adhered muscle tissue, according to an embodiment.

Referring now to FIG. 8, it may be preferred in at least one embodiment to attach muscle tissue, such as muscle tendons 800 and 802, to a sub-dermal strut 804 permanently anchored to a remnant bone 806. As shown in FIG. 8, multiple tendons or other muscle tissues may be attached to strut 804, or alternatively a single tendon may be adhered to the implant. Further, sub-dermal strut 804 may include at least one strain sensor 808 and a transmitter 810 for communicating sensed strain data to a controller (not shown). The advantages of a system 100 incorporating attached muscle tissue and strain gauge measurements include: (1) the muscle may act on the remnant bone to exert some control over induced moments (rotation); (2) if two muscles are balanced, which is to say attached to opposing sub-dermal struts, the two muscles could be exerted simultaneously with large forces in an isometric exercise, thereby maintaining muscle condition; (3) in combination with strain sensors and transmitters mounted to one or more sub-dermal strut, the action of adhered muscles could be detected and transmitted to an external robotic prosthesis, via a controller/control system, and the prosthesis would act on received signals to implement motion. This third advantage is an improvement over current systems used to relay neural signals to a prosthesis, wherein cortical implants are often employed.

Figure 9:
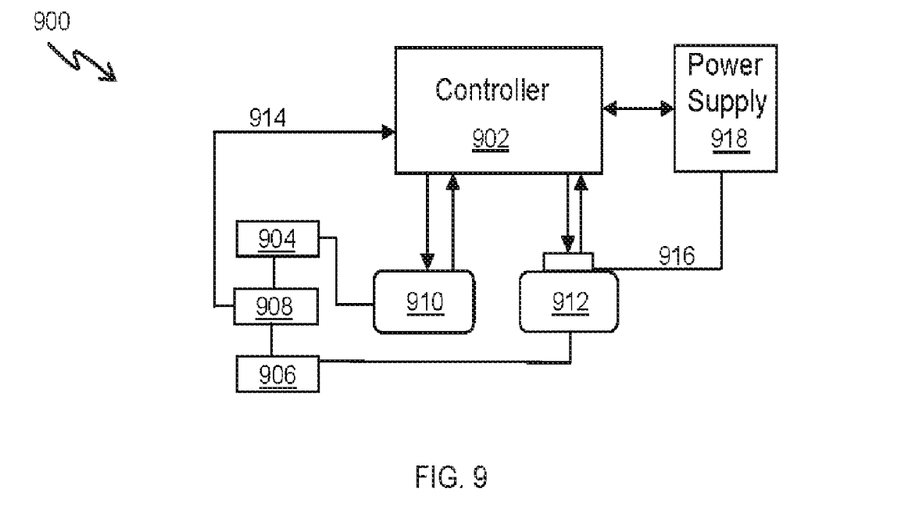
FIG. 9 is a schematic of a control system, according to an embodiment.

With regard to a controller and control system, in FIG. 9 a simplified schematic of a control system 900 of the present application is presented. Control system 900 may be used to monitor system parameters, control magnetic forces and ensure safe, reliable operation of a prosthetic device. A controller 902 is in electronic communication with one or more sensor suites which include both strain gauges 904, 906 and a transmitter 908. Strain gauges and transmitters (e.g. strain gauge 904 and transmitter 908) may be any of a type well known in the art for monitoring stress-strain forces as those forces are translated from one structure (e.g. prosthetic device 910) to a second structure (e.g. remnant bone 806 in FIG. 8). Further, a sensor suite may include position sensors (not shown) to monitor prosthesis position relative to an amputation point, and to monitor prosthesis movement. Strain gauges 904, 906 may be oriented to detect induced forces in a variety of directions (e.g. lateral, vertical), and no two sensors need necessarily be oriented in the same or similar direction. Placement and orientation of strain gauges and transmitters is one part of the optimization process required to ensure maximum system 100 performance.

Still referring to FIG. 9, strain gauges 904, 906 detect loads induced in one or more prosthetic devices, e.g. devices 910 and 912, and subsequently transmit load data, via transmitter 908, to a controller 902. In one embodiment, controller 902 is positioned within a prosthetic device 910, 912. In yet another embodiment, controller 902 is remotely located. In either instance, data may be transferred to and from controller 902 via control lines such as line 914, and control directions may be passed to a prosthetic device, 912, via line 916. Alternatively, data may be transmitted via radio frequency transmissions. Input data may include stress-strain (load data), position data, as well as periodic "health and welfare" data (e.g. operating temperature, voltage level, etc.) from various control system 900 components and magnets. Output data may include commands sent to various locations to ensure effective operation. In addition to commands sent to the prosthetic device, e.g. device 912, commands may be sent by controller 902 to a magnet drive mechanism (not shown) co-located with one or more electromagnets.

In addition to strain gauges 904, 906, a transmitter 908, and a controller 902, control system 900 may include a power supply 918. Power supply 918 may be required to provide current to magnets of system 100 if electromagnets are used and to power controller 902. As with controller 902, power supply 918 may be remotely located away from, but in relative proximity to, prosthetic device 910, 912, or it may be incorporated into the prosthesis design.

System 100 optimization and the corresponding control requirements will depend on multiple factors to include: whether the amputation or limb damage is partial or complete (whole limb amputation); the location of the prosthesis on the patient's body; corresponding loads induced into the prosthesis and skeletal structure; osseointegration concerns and a desire to ensure acceptance of foreign matters by the body, etc.

Figure 10:
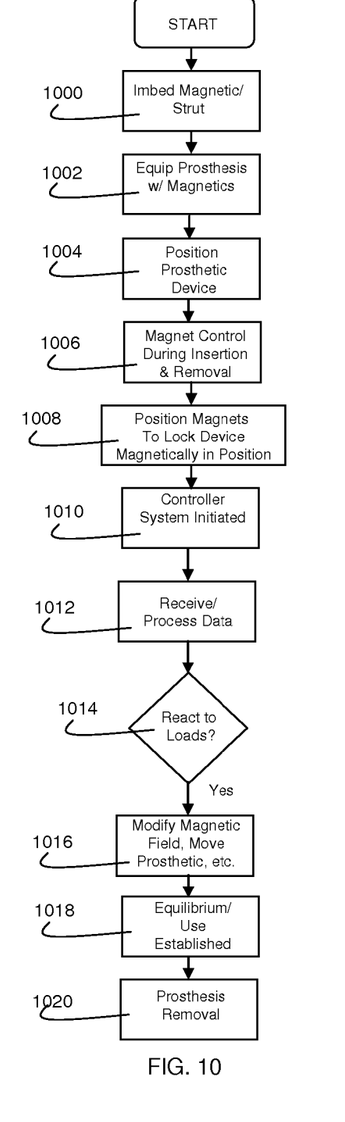
FIG. 10 is a flow chart of a method for implementing a prosthesis system, according to an embodiment.

Referring to FIG. 10, in the operation of prosthesis system 100, discrete magnets which are mounted onto and/or into a sub-dermal strut are surgically embedded into the person and permanently anchored to a portion of a residual limb, block 1000. The strut is positioned beneath the surface of the skin such that there are no protrusions through the skin. Optimally, osseointegration occurs thereby ensuring acceptance of the materials by the body and a strengthening of the magnet to bone interface. Concurrently, a prosthetic device is equipped with individual magnets and magnet sets, some or all of which may be electromagnets, block 1002.

Figure 11:
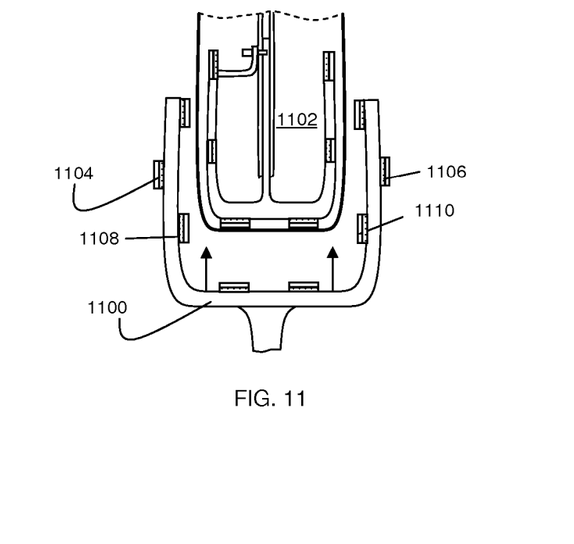
FIG. 11 is a cross-sectional view of a disengaged prosthetic socket, according to an embodiment.
Figure 12:
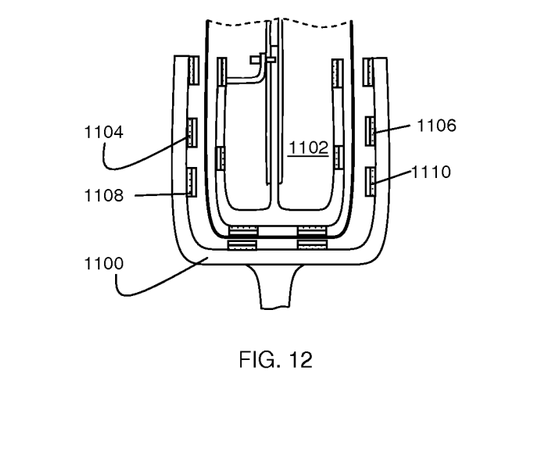
FIG. 12 is a cross-sectional view of an engaged prosthetic socket, according to an embodiment.

As a next step, block 1004, the prosthetic device is moved into position to interface with the residual limb of the person. In this context, the term "residual limb" connotes the point of skeletal structure deformation, whether by amputation, birth defect, injury, etc. Magnets are deployed in both the residual limb and prosthetic device in such a way as to achieve stability with respect to the approach of the prosthetic device to the limb, rotation of the prosthetic device during coupling and use, controlled sliding or lateral movement of the prosthetic device, and reaction to loads induced into the prosthetic device and residual limb. In particular, and referring for a moment to FIGS. 11 and 12, as the prosthetic device/prosthetic socket (e.g. socket 1100) is introduced to the residual limb 1102, certain of the magnets are controlled (block 1006) to reduce corresponding magnetic fields and allow for easy installation (and removal in the alternative). For example, magnets 1104 and 1106 may be mechanically rotated out of alignment with magnets 1108 and 1110 respectively. A similar effect can be achieved with electromagnets, whereby the current to the magnets is reduced/modified to minimize the magnetic field. As shown in FIG. 12, once the prosthetic socket 1100 is properly positioned and spaced with respect to the residual limb 1102, magnets 1104 and 1106 are mechanically returned to align with magnets 1108 and 1110, or in the case of electromagnets the current is modified to reinitialize or strengthen the magnetic field, thereby locking the prosthetic socket 1100 into position, block 1008.

The orientation, strength and direction of the magnetic fields may change during use, according to commands from the controller. A control system is initialized and made operational, calibrated, and positioned either within the prosthetic device or in a remote location on the body of the person, block 1010.

Once the prosthesis is positioned for use, the control system continually monitors load and position sensors and processes the received data, block 1012. Based on input data, the controller "decides" if the prosthesis is moving or is required to react/absorb/dampen an induced load, and if the magnetic forces/fields need to be altered in order to maintain prosthesis coupling, stability and use, block 1014. If reaction to load inducement and prosthesis movement is required, the controller may send commands to the power supply to vary the current level, and may command changes to the magnets such as direction of current flow, magnet rotation, etc., block 1016. Ultimately, equilibrium and stability are achieved giving the patient unencumbered use of the prosthesis through indirect coupling or a combination of direct (minimal) and indirect coupling, block 1018. Removal of the prosthesis can be achieved by altering the magnetic field attractions such that coupling is severed and the prosthesis can be moved away from the residual limb, block 1020.

Changes may be made in the above methods, devices and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, device and structure, which, as a matter of language, might be said to fall therebetween.

What is claimed is:

1. A prosthesis system comprising:
a prosthetic limb having a prosthetic socket, the prosthetic socket including a proximal end, a distal end, a rigid structure disposed at the distal end, and a sleeve extending from the
distal end towards the proximal end and forming an opening at the proximal end to receive a residual limb, the rigid structure having a portion extending from the distal end toward the proximal end;

a sub-dermal strut configured for placement under the skin of the residual limb, the sub-dermal strut having a distal end and a proximal end and a flange extending from the distal end of the sub-dermal strut toward the proximal end of the sub-dermal strut;

an anchoring post attached to the sub-dermal strut and configured to anchor to a bone of the residual limb;

at least two discrete magnets, one of the discrete magnets being disposed on the flange and the other discrete magnet being disposed at the distal end of the sub-dermal strut;

a magnet set including at least two set magnets disposed on the portion of the rigid structure, the at least two magnets being arranged and configured to generate magnetic fields extending inwardly toward a longitudinal center axis of the sleeve; and an individual magnet disposed on the rigid structure.

2. The prosthesis system of claim 1, wherein the magnet set and/or the individual magnet include electromagnets.

3. The prosthesis system of claim 2, further comprising a controller for dynamic control of magnetic forces through current control of electromagnets in response to sensory data.

4. The prosthesis system of claim 3, further comprising: at least one strain sensor mounted on the sub-dermal strut; and at least one transmitter electrically connected to the strain sensor for receiving a signal from the strain sensor and for transmitting the signal to the controller.

5. The prosthesis system of claim 1, further comprising
a socket liner; and
a compliant coupling layer for contacting the socket liner, the compliant coupling layer being disposed at the rigid structure.

6. The prosthesis system of claim 5, wherein the compliant coupling layer is selected from a group consisting of: a fluid bladder; a gel bladder; a foam; an elastomer; a lubricated interface; and a compliant truss structure.

7. The prosthesis system of claim 1, wherein the prosthetic limb is selected from a group consisting of a partial limb prosthesis, a whole limb prosthesis and an orthopedic correction prosthesis.

8. The prosthesis system of claim 1, wherein the at least two discrete magnets are shaped to match a contour of the residual limb.

9. The prosthesis system of claim 1, wherein the sub-dermal strut is disposed in the sleeve to position the discrete magnet on the flange between the at least two set magnets of the magnet set.

10. The prosthesis system of claim 9, wherein the sub-dermal strut is further disposed to substantially align the individual magnet with the discrete magnet disposed at the distal end of the sub-dermal strut for the magnets to repel one another.

11. A prosthesis system comprising:
a prosthetic limb having a prosthetic socket for receiving a residual limb therein;
a magnet set disposed on the prosthetic socket, the magnet set having magnetic fields that generate a magnetic potential well and at least one rotatable magnet rotatable relative to the prosthetic socket to reduce the magnetic fields;
a sub-dermal strut configured for placement under the skin of the residual limb;
an anchoring post attached to the sub-dermal strut and configured to anchor to a bone of a residual limb;
a first discrete magnet attached to the sub-dermal strut and positioned within the magnetic potential well generated by the magnet set;
a second discrete magnet attached to the sub-dermal strut; and
an individual magnet positioned on the prosthetic socket and aligned with the first magnet to repel the first magnet.

12. The prosthesis of claim 11, further comprising
a compliant coupling layer disposed at the prosthetic socket; and
a socket liner configured to protect a skin of the residual limb, wherein the compliant coupling layer and the socket liner are configured to interface to transfer load between the residual limb and the prosthetic socket.

13. The prosthesis system of claim 11, further comprising
a measuring means for measuring a strain induced in the residual limb and generating measured strain data;
a transmitting means for transmitting the measured strain data; and
a controlling means for receiving transmitted measured strain data and for utilizing transmitted measured strain data to control the prosthetic socket.

* * * * *